United States Patent
Deamer et al.

(10) Patent No.: US 12,325,011 B2
(45) Date of Patent: Jun. 10, 2025

(54) METHODS AND DEVICES FOR NON-ENZYMATIC NUCLEIC ACID SYNTHESIS

(71) Applicant: The Regents of the University of California, Oakland, CA (US)

(72) Inventors: David W. Deamer, Santa Cruz, CA (US); Gabriel Mednick, Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 1004 days.

(21) Appl. No.: 17/288,356

(22) PCT Filed: Oct. 30, 2019

(86) PCT No.: PCT/US2019/058839
§ 371 (c)(1),
(2) Date: Apr. 23, 2021

(87) PCT Pub. No.: WO2020/092543
PCT Pub. Date: May 7, 2020

(65) Prior Publication Data
US 2021/0379554 A1  Dec. 9, 2021

Related U.S. Application Data

(60) Provisional application No. 62/754,418, filed on Nov. 1, 2018.

(51) Int. Cl.
*B01J 19/00* (2006.01)
*C07H 21/02* (2006.01)

(52) U.S. Cl.
CPC .......... *B01J 19/0046* (2013.01); *C07H 21/02* (2013.01); *B01J 2219/00495* (2013.01); *B01J 2219/00511* (2013.01); *B01J 2219/00538* (2013.01); *B01J 2219/0059* (2013.01); *B01J 2219/00596* (2013.01); *B01J 2219/00626* (2013.01); *B01J 2219/00716* (2013.01); *B01J 2219/00722* (2013.01)

(58) Field of Classification Search
CPC .......... B01J 19/0046; B01J 2219/00538; B01J 2219/00722; C07H 21/02
See application file for complete search history.

(56) References Cited

U.S. PATENT DOCUMENTS

| | | |
|---|---|---|
| 7,772,390 B1 | 8/2010 | Deamer |
| 2003/0162210 A1 | 8/2003 | Chetverin et al. |
| 2005/0282188 A1 | 12/2005 | Haeberli et al. |
| 2006/0154248 A1 | 7/2006 | Mcgrew et al. |
| 2010/0197509 A1 | 8/2010 | Chetverin et al. |
| 2016/0229882 A1 | 8/2016 | Deamer et al. |

FOREIGN PATENT DOCUMENTS

| | | |
|---|---|---|
| GB | 1549814 A | 8/1979 |
| WO | 2009136623 A1 | 11/2009 |

OTHER PUBLICATIONS

Daud, W.R.W., Handbook of Industrial Drying, 2006, 3rd edition, CRC Press, p. 203-213. (Year: 2006).*
Tang et al., Encyclopedia of Agricultural, Food, and Biological Engineering, 2003, Marcel Dekker Inc., p. 211-214. (Year: 2003).*
Aronin (2006) "Target selectivity in mRNA silencing" Gene Ther. 13(6):509-516.
Grunweller et al. (2005) "RNA Interference as A Gene-Specific Approach for Molecular Medicine" Curr Med Chem. 12(26):3143-3161.
Pekaraik et al. (2005) "Design of shRNAs for RNAi—A lesson from pre-miRNA processing: Possible clinical applications" Brain Res Bull. 68(1-2):115-120.
Pushparaj et al. (2006) "Short Intefering RNA (siRNA) As A Novel Therapeutic" Clin Exp Pharmacal Physiol. 33(5-6):504-510.
Xie et al. (2006) "Harnessing in vivo siRNA delivery for drug discovery and therapeutic development" Drug Discov Today. 11(1-2):67-73.

* cited by examiner

*Primary Examiner* — Jonathan S Lau
(74) *Attorney, Agent, or Firm* — Brian E. Davy; Bozicevic, Field & Francis LLP

(57) ABSTRACT

Provided are methods for non-enzymatically synthesizing nucleic acids. The methods include submerging a first portion of the outer surface of a cylinder in a non-enzymatic nucleic acid synthesis reaction mixture. The reaction mixture has a pH of 4 or less and includes an organizing matrix reagent and monophosphate nucleotides. The methods further include rotating the cylinder about its axis of radial symmetry so that the first portion of the outer surface of the cylinder is no longer submerged in the reaction mixture, thereby providing a thin film of the reaction mixture on the first portion of the outer surface of the cylinder. The methods further include heating and drying the thin film to form phosphodiester bonds between the monophosphate nucleotides of the thin film. Also provided are devices that find use, e.g., in practicing the methods of the present disclosure.

12 Claims, 4 Drawing Sheets

METHODS AND DEVICES FOR NON-ENZYMATIC NUCLEIC ACID SYNTHESIS

CROSS-REFERENCE TO RELATED APPLICATIONS

This application claims the benefit of U.S. Provisional Patent Application No. 62/754,418 filed Nov. 1, 2018, which application is incorporated herein by reference in its entirety.

INTRODUCTION

Nucleic acids find use in a variety of different applications including, but not limited to, research reagents, diagnostic agents and therapeutic agents. A variety of different protocols have been developed to synthesize nucleic acids. However, there is continued interest in the identification of new ways to synthesize nucleic acid.

Non-enzymatic nucleic acid synthesis approaches have been developed, including anhydrous heating of nucleotides (Verlander et al., *J. Mol. Evol.* (1973) 2:303), cycles of heating and drying (Usher, D. A. *Science* (1977) 196:311), as well as studying the impact of amphiphilic structures (Walde, P. *Orig Life Evol Biosph.* April 27 (2006); Deamer, D. W. and G. L. Barchfeld. (1982) *J. Mol. Evol.* 18:203; and Szostak J. W., Bartel, D. P. and Luisi, P. L. *Nature* (2001) 409:387).

Condensation of activated mononucleotides also has been employed for non-enzymatic synthesis. Imidazole esters of mononucleotides assemble on RNA templates to produce complementary RNA strands up to 40-50 nucleotides in length (Inoue T, and Orgel, L. E. *Science* (1983) 219:859; and Orgel, L. *Orig. Life Evol. Biosphere* (1997) 28:227). Mineral surfaces of montmorillonite clay organize imidazole-activated mononucleotides and synthesize RNA strands up to 50-mers in the absence of templates (Huang, W. and Ferris J. P. *Chem. Commun.* (2003) 21:1458; and Ferris, *J. Orig. Life Evol. Biosphere* (2002) 32:311). RNA oligomers of up to 14 nucleotides in length spontaneously assemble in the absence of templates or organizing surfaces when activated mononucleotides are concentrated in the eutectic phase of frozen reaction mixtures (Kanavarioti et al., *Astrobiology* (2002) 1:271).

Unfortunately, synthesis of nucleic acids as reported above has met with limited success, and new approaches for non-enzymatically synthesizing nucleic acids are needed. The present disclosure addresses this and other needs.

SUMMARY

Provided are methods for non-enzymatically synthesizing nucleic acids. The methods include submerging a first portion of the outer surface of a cylinder in a non-enzymatic nucleic acid synthesis reaction mixture. The reaction mixture has a pH of 4 or less and includes an organizing matrix reagent and monophosphate nucleotides. The methods further include rotating the cylinder about its axis of radial symmetry so that the first portion of the outer surface of the cylinder is no longer submerged in the reaction mixture, thereby providing a thin film of the reaction mixture on the first portion of the outer surface of the cylinder. The methods further include heating and drying the thin film to form phosphodiester bonds between the monophosphate nucleotides of the thin film. Further, methods of purifying the synthesized nucleic acid as well as methods for making nucleic acids having sense and anti-sense sequences for making double stranded nucleic acids are provided. Also provided are devices that find use, e.g., in practicing the methods of the present disclosure.

DETAILED DESCRIPTION

Figure 1:
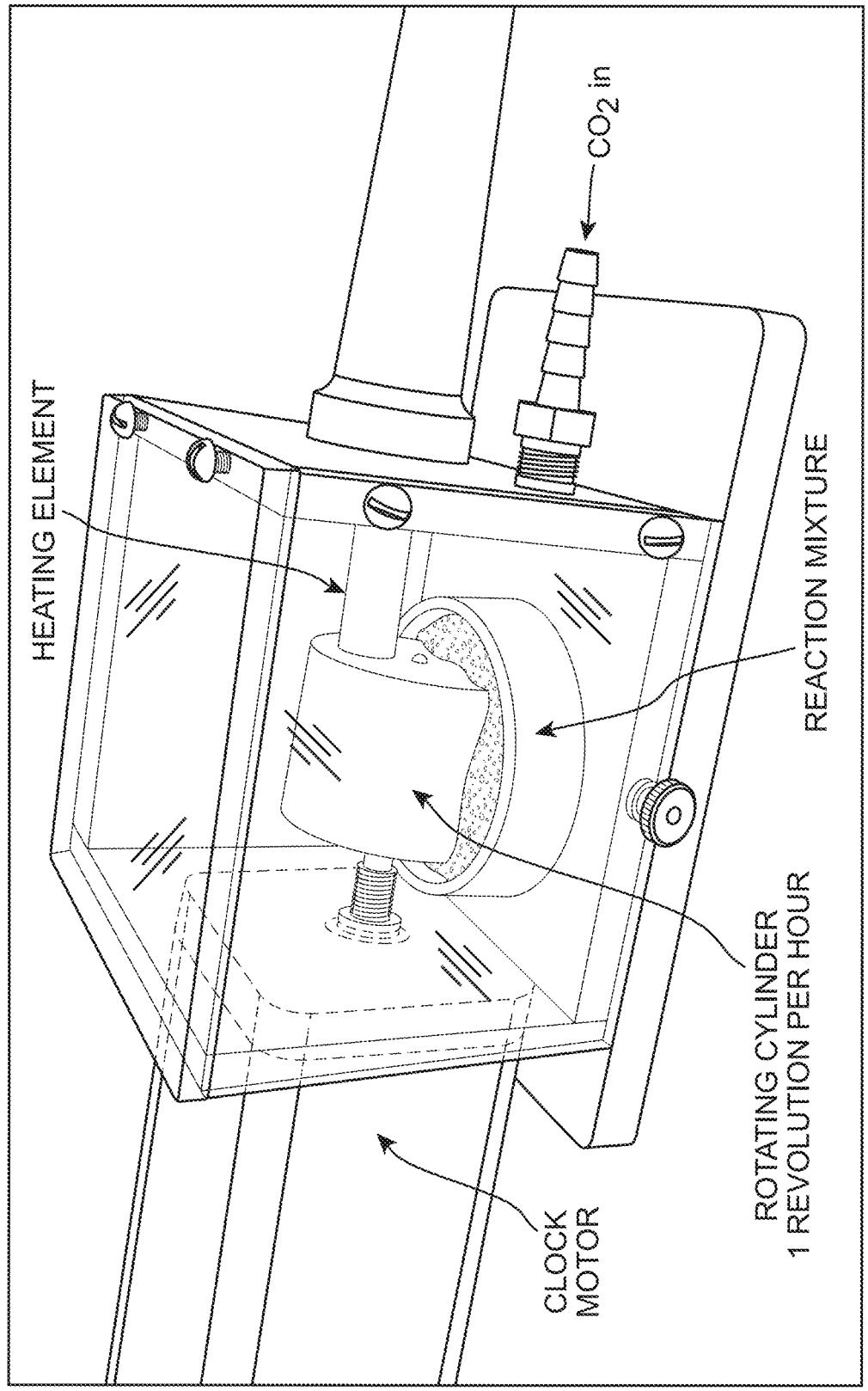
FIG. 1 A photograph of a device for non-enzymatic nucleic acid synthesis according to one embodiment of the present disclosure.

Provided are methods for non-enzymatically synthesizing nucleic acids. The methods include submerging a first portion of the outer surface of a cylinder in a non-enzymatic nucleic acid synthesis reaction mixture. The reaction mixture has a pH of 4 or less and includes an organizing matrix reagent and monophosphate nucleotides. The methods further include rotating the cylinder about its axis of radial symmetry so that the first portion of the outer surface of the cylinder is no longer submerged in the reaction mixture, thereby providing a thin film of the reaction mixture on the first portion of the outer surface of the cylinder. The methods further include heating and drying the thin film to form phosphodiester bonds between the monophosphate nucleotides of the thin film. Also provided are devices that find use, e.g., in practicing the methods of the present disclosure.

Before the methods and devices of the present disclosure are described in greater detail, it is to be understood that the methods and devices are not limited to particular embodiments described, as such may, of course, vary. It is also to be understood that the terminology used herein is for the purpose of describing particular embodiments only, and is not intended to be limiting, since the scope of the methods and devices will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and devices. The upper and lower limits of these smaller ranges may independently be included in the smaller ranges and are also encompassed within the methods and devices, subject to any specifically excluded limit in the stated range. Where the stated range includes one or both of the limits, ranges excluding either or both of those included limits are also included in the methods and devices.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods and devices belong. Although any methods and devices similar or equivalent to those described herein can also be used in the practice or testing of the methods and devices, representative illustrative methods and devices are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods and devices are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and devices, which are, for clarity, described in the context of separate embodiments, may also be provided in combination in a single embodiment. Conversely, various features of the methods and devices, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods and devices and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

The present disclosure provides methods for non-enzymatically synthesizing nucleic acids. The methods include submerging a first portion of the outer surface of a cylinder in a non-enzymatic nucleic acid synthesis reaction mixture. The reaction mixture has a pH of 4 or less and includes an organizing matrix reagent and monophosphate nucleotides. The methods further include rotating the cylinder about its axis of radial symmetry so that the first portion of the outer surface of the cylinder is no longer submerged in the reaction mixture, thereby providing a thin film of the reaction mixture on the first portion of the outer surface of the cylinder. The methods further include heating and drying the thin film to form phosphodiester bonds between the monophosphate nucleotides of the thin film. Aspects of the methods will now be described in greater detail.

The present disclosure is based in part on the ability to non-enzymatically synthesize nucleic acids by dehydrating a reaction mixture that includes an organizing matrix reagent and monophosphate nucleotides, where the dehydrating drives the synthesis reaction. The methods may include a single dehydration step, or the methods may include subjecting the reaction mixture to one or more cycles of hydration and dehydration. An example organizing matrix reagent that may be employed includes one or more amphiphilic compounds which concentrate and organize the reactant mononucleotides within multilamellar sheets during evaporation to dryness. Non-enzymatic amphiphilic compound-mediated nucleic acid synthesis is described, e.g., in U.S. Pat. No. 7,772,390, the disclosure of which is incorporated herein by reference in its entirety for all purposes. Also by way of example, the organizing matrix reagent may be a salt (e.g., a monovalent salt) that concentrates and organizes the reactant mononucleotides into a eutectic phase that causes them to form stacks (sometimes referred to as "pre-polymers") during evaporation to dryness. Non-enzymatic salt-mediated nucleic acid synthesis is described, e.g., in US Patent Application Publication No. US 2016/0229882, the disclosure of which is incorporated herein by reference in its entirety for all purposes.

According to the present disclosure, dehydrating the reaction mixture, or subjecting the reaction mixture to one or more cycles of hydration and dehydration, is achieved using a rotating cylinder. The cylinder is rotated to provide a thin film of the reaction mixture on at least a first portion of the outer surface of the cylinder. The thin film is heated and dried such that phosphodiester bonds form between the monophosphate nucleotides of the thin film. As will be appreciated with the benefit of the present disclosure, one or more revolutions of the cylinder may correspond to one or more cycles of hydration and dehydration, thereby providing improved methods and devices for convenient non-enzymatic nucleic acid synthesis.

Any of the methods of the present disclosure may be performed using the devices of the present disclosure. Such devices are described in detail herein below.

As summarized above, the methods of the present disclosure include submerging a first portion of the outer surface of a cylinder in a non-enzymatic nucleic acid synthesis reaction mixture. The manner in which the first portion of the outer surface of the cylinder is submerged in the reaction mixture may vary. In certain aspects, the outer surface of the cylinder is not initially in contact with the reaction mixture and the cylinder is lowered into the reaction mixture to a desired depth to submerge the first portion in the reaction mixture. In other aspects, a portion other than the first portion of the cylinder is submerged in the reaction mixture, and submerging the first portion in the reaction mixture includes rotating the cylinder about its axis of radial symmetry such that the first portion rotates into the reaction mixture.

The depth at which the first portion (or one or more portions) of the cylinder is submerged in the reaction mixture may vary. The depth is such that upon rotating the first portion out of the reaction mixture, a thin film of the reaction mixture is provided. In some embodiments, the cylinder is submerged in the reaction mixture at a depth of from about 3% to 30% of the diameter of the cylinder, such as from about 4% to 25%, from about 5% to 20%, from about 5% to 15%, or from about 5% to 10% of the diameter of the cylinder. In some embodiments, when carrying out the methods, the distance between the radial axis of the cylinder and the surface of the reaction mixture may be adjusted to maintain a suitable/desired depth of submersion of the cylinder in the reaction mixture, e.g., to account for evaporation of liquid components (e.g., water) present in the reaction mixture.

The methods include rotating the cylinder about its axis of radial symmetry so that the first portion of the outer surface of the cylinder is no longer submerged in the reaction mixture. In some embodiments, the methods include continuously rotating the cylinder about its axis of radial symmetry to rotate the first portion into the reaction mixture and rotate the first portion out of the reaction mixture. In certain aspects, the methods include rotating the cylinder about its axis of radial symmetry to rotate the first portion into the reaction mixture and rotate the first portion out of the reaction mixture, where the rotation is discontinuous. As used herein, "discontinuous" means the cylinder ceases to rotate at least once at one or more selected positions for a desired period of time.

In some embodiments, the methods further include, subsequent to the heating and drying, re-submerging the first portion of the outer surface of the cylinder in the reaction mixture. The manner in which the first portion is re-submerged in the reaction mixture may vary, and may include any of the approaches described above such as lowering the cylinder such that the first portion is lowered into the reaction mixture, or rotating the cylinder about its axis of radial symmetry to rotate the first portion into the reaction mixture. In certain aspects, the methods include continuously rotating the cylinder about its axis of radial symmetry to rotate the first portion into the reaction mixture, rotate the first portion out of the reaction mixture, and rotate the first portion back into the reaction mixture. In some embodiments, the methods include rotating the cylinder about its axis of radial symmetry to rotate the first portion into the reaction mixture, rotate the first portion out of the reaction mixture, and rotate the first portion back into the reaction mixture, where the rotation is discontinuous.

In certain aspects, the methods include rotating the cylinder through one or more revolutions. For example, the cylinder may be rotated about its axis of symmetry (continuously or discontinuously) to rotate the first portion of the outer surface of the cylinder into the reaction mixture, rotate the first portion out of the reaction mixture, rotate the cylinder while the thin film is being heated and dried, and rotate the first portion back into the reaction mixture to complete a revolution. The cylinder may be rotated continuously or discontinuously through one or any desired number of revolutions. For example, the cylinder may be rotated continuously or discontinuously through from 1 to 1000 revolutions, from 1 to 500 revolutions, from 1 to 250 revolutions, from 1 to 200 revolutions, from 1 to 150 revolutions, from 1 to 100 revolutions, from 1 to 90 revolutions, from 1 to 80 revolutions, from 1 to 70 revolutions, from 1 to 60 revolutions, from 1 to 50 revolutions, from 1 to 40 revolutions, from 1 to 30 revolutions, from 1 to 24 revolutions, from 1 to 20 revolutions, from 1 to 10 revolutions, from 1 to 9 revolutions, from 1 to 8 revolutions, from 1 to 7 revolutions, from 1 to 6 revolutions, from 1 to 5 revolutions, from 1 to 4 revolutions, from 1 to 3 revolutions, from 1 to 2 revolutions (e.g., 2 revolutions), or 1 revolution.

The number of revolutions may be selected to obtain a desired yield of non-enzymatically synthesized nucleic acids. As will be appreciated, one revolution of the cylinder may correspond to one cycle (or "round") of non-enzymatic nucleic acid synthesis, where the yield of synthesized nucleic acids may be increased as desired by performing 2 or more cycles as compared to the yield obtained from a single cycle.

The rotational speed of the cylinder may vary. For example, when the method includes re-submerging the first portion of the outer surface of the cylinder in the reaction mixture by rotating the first portion back into the reaction mixture, a suitable rotational speed will be one in which the thin film has been sufficiently heated and dried (that is, phosphodiester bonds have formed) prior to being re-submerged in the reaction mixture. Conditions that promote rapid drying of the thin film (e.g., higher temperature, higher air flow, lower humidity, and/or the like) permit a higher rotational speed as compared to conditions which result in slower drying of the thin film, e.g., lower temperature, lower air flow, higher humidity, and/or the like. As such, the rotational speed may be selected based on the conditions to which the thin film is exposed, and vice versa. In some embodiments, the cylinder is rotated at a rotational speed of from 1 revolution per 10 minutes to 1 revolution per 180 minutes, from 1 revolution per 20 minutes to 1 revolution per 120 minutes, from 1 revolution per 30 minutes to 1 revolution per 90 minutes, from 1 revolution per 40 minutes to 1 revolution per 80 minutes, or from 1 revolution per 50 minutes to 1 revolution per 70 minutes, e.g., 1 revolution per about 1 hour.

The components, ratios thereof, and concentrations thereof in the reaction mixture may vary. Non-limiting examples of such components, ratios thereof, and concentrations thereof include any of those described in U.S. Pat. No. 7,772,390 and US Patent Application Publication No. US 2016/0229882, the disclosures of which are incorporated herein by reference in their entireties for all purposes.

As summarized above, the organizing matrix reagent may include one or more amphiphilic compounds. By "amphiphilic" is meant the compound comprises a polar water-soluble group attached to a water-insoluble hydrocarbon chain. Non-limiting examples of amphiphilic compounds which may be employed include phospholipids, lysophosphatidylcholine, mixtures of dodecanoic acid with its monoglyceride, and any combinations thereof. The reaction mixture may be designed to have a selected mass ratio of monophosphate nucleotides to amphiphilic compounds. In certain aspects, the selected mass ratio of monophosphate nucleotides:amphiphilic compounds is from 1:1 to 3:1, such as from about 1.25:1 to 2.75:1, from 1.5:1 to 2.5:1, or from 1.75:1 to 2.25:1, e.g., about 2:1.

As summarized above, the organizing matrix reagent may include one or more monovalent salts. In certain aspects, the one or more monovalent salts includes a halide salt. Suitable halide salts include, but are not limited to, ammonium halide salts. Ammonium halide salts which may be employed include $NH_4F$, $NH_4Cl$, $NH_4Br$, $NH_4I$, and any combination thereof. In some embodiments, the organizing matrix reagent includes ammonium chloride ($NH_4Cl$). In certain aspects, the organizing matrix reagent includes one or more monovalent salts selected from the group consisting of: NaF, CsCl, NaBr, $NaClO_4$, NaCl, KCl, $NH_4Cl$, and any combination thereof. When the organizing matrix reagent includes one or more monovalent salts, the concentration of the one or more monovalent salts may vary. In some embodiments, the one or more monovalent salts is present in the reaction mixture at a concentration of from 0.025 M to 3 M, such as from 0.05 M to 2 M, or from 0.75 M to 1 M, e.g., from 0.1 M to 0.5 M.

In certain aspects, the reaction mixture has a pH of 4 or less. For example, the reaction mixture may have a pH of from 2 to 4, such as a pH of from 2 to 3, e.g., a pH of about 2.5.

As summarized above, the methods of the present disclosure include heating and drying the thin film to form phosphodiester bonds between the monophosphate nucleotides of the thin film. Drying and heating the thin film drives the synthesis reaction and provides the requisite activation energy. A variety of approaches may be used to heat the thin film. In certain aspects, the thin film is heated using a heating element disposed adjacent the outer surface of the cylinder, where the heating element is disposed on the side opposite the thin film from the outer surface of the cylinder. In some embodiments, heating the thin film includes heating the inner surface of the cylinder, where the cylinder materials are selected to be sufficiently conductive such that the heat at the inner surface of the cylinder is conducted to the outer surface of the cylinder to heat the thin film disposed thereon. The inner surface of the cylinder may be heated using a heating element thermally coupled (e.g., in contact with or disposed in sufficient proximity) to the inner surface of the cylinder. One example of such a configuration is shown in FIG. 1, where a heating element is partially inserted into an internal portion of a cylinder in sufficient proximity to the inner surface of the cylinder to heat the inner surface of the cylinder, where the heat at the inner surface of the cylinder is conducted to the outer surface of the cylinder to heat the thin film disposed thereon. The temperature to which the thin film is heated is sufficiently high to provide the activation energy necessary for non-enzymatic phosphodiester bond formation. In certain aspects, the thin film is heated to a temperature of from 60° C. to 100° C., from 65° C. to 95° C., from 70° C. to 90° C., or from 75° C. to 85° C., e.g., about 80° C.

Drying the thin film may include only the heating of the thin film. In other aspects, one or more additional suitable approaches for drying a thin film of a reaction mixture on a surface is employed in addition to the heating of the thin film. In some embodiments, in addition to heating the thin film, a gas is flowed over the surface of the outer surface of the cylinder/thin film to facilitate drying of the thin film. Alternatively, or additionally, the humidity of the environment in which the heating and drying takes place may be controlled to facilitate drying of the thin film. For example, when the submerging, heating and drying, etc. is performed in a hermetically sealed chamber, a de-humidifier may be provided in the chamber to produce a low humidity within the chamber, thereby facilitating drying of the thin film.

The submerging, drying and heating (and optionally, any re-submerging or other steps) may be performed in an anaerobic environment. By "anaerobic environment" is meant that the submerging, drying and heating occur in the absence or substantially in the absence of oxygen. In some embodiments, the submerging, drying and heating are performed in a hermetically sealed chamber, and an anaerobic environment is provided within the chamber. The anaerobic environment may be provided, e.g., by flowing carbon dioxide ($CO_2$), an inert gas (e.g., nitrogen gas, argon gas, helium gas, and/or the like), or any combination thereof, into the chamber such that all or substantially all of the oxygen is removed from the chamber. In one example approach, one or more walls of the chamber may include one or more gas ports through which $CO_2$, an inert gas, and/or the like may be introduced into the chamber.

The methods of the present disclosure may be used to synthesize a variety of types of nucleic acids. In certain aspects, the reaction mixture includes only deoxyribonucleotides such that only deoxyribonucleic acid (DNA) is non-enzymatically synthesized. In other aspects, the reaction mixture includes only ribonucleotides such that only ribonucleic acid (RNA) is non-enzymatically synthesized. In still other aspects, the reaction mixture includes a mixture of deoxyribonucleotides and ribonucleotides such that nucleic acids that include both deoxyribonucleotide and ribonucleotide subunits are non-enzymatically synthesized. The reaction mixture may include naturally-occurring nucleotides only, non-naturally-occurring nucleotides only, or a combination of naturally-occurring nucleotides and non-naturally-occurring nucleotides. Non-naturally-occurring nucleotides of interest include, but are not limited to, one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, one or more dUTP (deoxyuridine triphosphate) nucleotides, or any other non-natural nucleotide feature that provides a desired functionality to the synthesized nucleic acids. In some embodiments, the reaction mixture includes nucleotides having a universal base, such as 2'-deoxyinosine and/or the like.

In certain aspects, the nucleic acids synthesized according to the present methods include oligonucleotides. As used herein, an "oligonucleotide" is a single-stranded multimer of nucleotides having from 2 to 200 nucleotides. In some embodiments, the non-enzymatically synthesized nucleic acids include oligonucleotides having from 5 to 150 nucleotides, from 5 to 125 nucleotides, from 5 to 110 nucleotides, from 5 to 100 nucleotides, from 5 to 90 nucleotides, from 5 to 80 nucleotides, from 5 to 70 nucleotides, from 5 to 60 nucleotides, from 5 to 50 nucleotides, from 5 to 40 nucleotides, or from 5 to 30 nucleotides. The non-enzymatically synthesized nucleic acids may include oligonucleotides having from 5 to 10, 10 to 20, 20 to 30, 30 to 40, 40 to 50, 50 to 60, 60 to 70, 70 to 80, 80 to 90, 90 to 100, 100 to 150, or 150 to 200 nucleotides, for example.

In some embodiments, the nucleic acids synthesized according to the present methods include small nucleic acid molecules, such as short interfering nucleic acid (siNA), short interfering RNA (siRNA), double-stranded RNA (dsRNA), micro-RNA (miRNA), and short hairpin RNA (shRNA). The terms "short interfering nucleic acid," "siNA," "short interfering RNA," "siRNA," "short interfering nucleic acid molecule," "short interfering oligonucleotide molecule," and the like, as used herein refer to any nucleic acid molecule capable of inhibiting or down regulating gene expression, for example by mediating RNA interference "RNAi" or gene silencing in a sequence-specific manner. Design of RNAi molecules, when given a target gene, is known and described in, e.g., US 2005/0282188 (which is incorporated herein by reference in its entirety for all purposes) as well as references cited therein. See also, e.g., Pushparaj et al. *Clin Exp Pharmacol Physiol.* 2006 33(5-6):504-10; Lutzelberger et al. *Handb Exp Pharmacol.* 2006 (173):243-59; Aronin et al. *Gene Ther.* 2006 13(6):509-16; Xie et al. *Drug Discov Today.* 2006 11(1-2): 67-73; Grunweller et al. *Curr Med Chem.* 2005 12(26):

3143-61; and Pekaraik et al. *Brain Res Bull.* 2005 68(1-2): 115-20, the disclosures of which are incorporated herein by reference in their entireties.

In some embodiments, the nucleic acids synthesized according to the present methods include short (or small) interfering RNA (siRNA). siRNA is the most commonly used RNA interference (RNAi) tool for inducing short-term silencing of protein coding genes. siRNA is a synthetic RNA duplex designed to specifically target a particular mRNA for degradation. siRNAs consist of two RNA strands, an anti-sense (or guide) strand and a sense (or passenger) strand, which form a duplex 19 to 25 bp in length with 3' dinucle-otide overhangs. siRNAs may be transfected into cells where the guide strand is loaded into the RNA-induced silencing complex, or RISC. This activated protein and nucleic acid complex can then elicit gene silencing by binding, through complementarity, to a single target mRNA sequence, thereby targeting it for cleavage and degradation.

According to the methods of the present disclosure, the non-enzymatic nucleic acid synthesis may occur on a nucleic acid template. In some embodiments, the nucleic acid template is a DNA template. In certain aspects, the nucleic acid template is an RNA template. A nucleic acid template may be provided to facilitate the synthesis of nucleic acids having a desired sequence, where the monophosphate nucleotides in the thin film preferentially line up on the nucleic acid template according to Watson-Crick base pairing. As just one example, when it is desirable to produce a strand of an siRNA for targeting a particular mRNA for degradation, a template having a sequence complementary to the desired siRNA strand sequence may be provided. In some embodiments, nucleic acids having different desired sequences may be produced in multiplex (i.e., in a single "run" of one or more cycles/cylinder revolutions), e.g., by providing two or more templates having distinct sequences complementary to the sequences of two or more nucleic acids that one desires to non-enzymatically synthesize.

When the non-enzymatic synthesis is templated, the manner in which the template nucleic acids are provided may vary. In certain aspects, the reaction mixture includes the template nucleic acids. In some embodiments, at least the first portion of the outer surface of the cylinder includes template nucleic acids disposed thereon. The manner in which the template nucleic acids are disposed on the at least the first portion of the outer surface of the cylinder may vary and depend, e.g., on the material from which the outer surface of the cylinder is made, e.g., metal, glass, ceramic, a polymer, plastic, and/or the like. One non-limiting example approach for disposing the template nucleic acids is to functionalize the outer surface of the cylinder by coating the at least the first portion of the outer surface of the cylinder (e.g., a glass outer surface) with silane-PEG-NHS and covalently linking the template nucleic acids through a reaction between the NHS groups and amine modified nucleotides that have been incorporated into the template nucleic acids.

The methods of the present disclosure may further include recovering non-enzymatically synthesized nucleic acids from the first portion of the outer surface of the cylinder. A variety of suitable recovery approaches are available. For example, when the methods include re-submerging the first portion of the outer surface of the cylinder in the reaction mixture under conditions in which the synthesized nucleic acids elute off of the first portion and into the reaction mixture, the synthesized nucleic acids may be recovered from the reaction mixture. As another example, upon completion of one or a desired number of synthesis cycles, the first portion of the outer surface of the cylinder may be submerged in a liquid which is not the reaction mixture, but rather a nucleic acid elution liquid (e.g., water, nucleic acid elution buffer or the like), and the synthesized nucleic acids may be recovered from the nucleic acid elution liquid. In this example, upon completion of the one or more desired synthesis cycles, a reservoir containing the reaction mixture could be replaced by a reservoir containing the nucleic acid elution liquid, or the reaction mixture in a reservoir could be removed and replaced with nucleic acid elution liquid. Recovery of the synthesized nucleic acids from the reaction mixture and/or elution liquid can be carried out by, e.g., ethanol precipitation, spin column purification (e.g., using a Zymo-Spin™ spin column), and/or the like. In certain aspects, where a template nucleic acid is used, the heating and drying step while facilitating synthesis of the complementary nucleic acid may also decrease hybridization between the synthesized nucleic acid and the template nucleic acid thereby facilitating elution of the synthesized nucleic acids when the cylinder is re-submerged into the reaction mixture or into a nucleic acid elution liquid.

The present disclosure also provide methods for isolating the synthesized nucleic acid by using two cylinders, where the two cylinders each include the template nucleic acid and where the template nucleic acid on one cylinder is used to synthesize a nucleic acid complementary to the template and the template nucleic acid on the other cylinder is used recover the synthesized nucleic acid by hybridization to the synthesized nucleic acid. This method is described below.

The methods disclosed herein, such as, in the preceding paragraphs, can be performed using a first cylinder, where the first cylinder is a cylinder described in the preceding paragraphs. For example, the template nucleic acid is covalently attached to the first portion of the outer surface of the first cylinder. The method includes submerging the first portion of the outer surface of the first cylinder in a non-enzymatic nucleic acid synthesis reaction mixture. The reaction mixture has a pH of 4 or less and includes an organizing matrix reagent and monophosphate nucleotides, as disclosed in the preceding paragraphs. The method further include rotating the first cylinder about its axis of radial symmetry so that the first portion of the outer surface of the first cylinder is no longer submerged in the reaction mixture, thereby providing a thin film of the reaction mixture on the first portion of the outer surface of the first cylinder. The method further includes heating and drying the thin film to form phosphodiester bonds between the monophosphate nucleotides of the thin film to synthesize a nucleic acid complementary to the template nucleic acid. Subsequent to the heating and drying, the method includes re-submerging the first portion of the outer surface of the first cylinder in the reaction mixture to release the synthesized nucleic acid into the reaction mixture. The steps of submerging, heating and drying, and re-submerging may be as described above. In certain aspects, the first cylinder may be heated to decrease likelihood of retention of the synthesized nucleic acid on the first cylinder via hybridization to the template nucleic acid present on the first cylinder and increase elution of the synthesized nucleic acid into the reaction mixture. For example, the first cylinder may be heated during an initial period during the re-submerging step to decrease hybridization between the template nucleic acid and the synthesized nucleic acid and subsequently the first cylinder may no longer be heated to facilitate formation of hydrogen bonded pairing between mononucleotides in the reaction mixture and the template nucleic acid for synthesizing additional copies of the nucleic acids. Alternatively, the heating and drying step provides residual increase in temperature at the outer surface of the first cylinder sufficient to decrease hybridization between the template nucleic acid and the synthesized nucleic acid and re-submerging the cylinder results in release of the synthesized nucleic acid followed by cooling of the outer surface such that mononucleotides base pair with the template nucleic acid on the outer surface of the cylinder.

The method further includes capturing the synthesized nucleic acid from the reaction mixture by submerging a first portion of the outer surface of a second cylinder into the reaction mixture. The first portion of the outer surface of the second cylinder includes the template nucleic acid covalently attached thereto. The second cylinder is at a temperature suitable for hybridization between the template nucleic acid and the synthesized nucleic acid to capture the synthesized nucleic acid. The temperature suitable for hybridization between the template nucleic acid and the synthesized nucleic acid may be room temperature or any temperature at which the synthesized nucleic acid binds to the template nucleic acid while the mononucleotides or partially synthesized nucleic acids do not bind in significant amounts. In certain aspects, the second cylinder may be heated to increase the temperature of the outer surface of the second cylinder to a temperature suitable for hybridization between the template nucleic acid and the synthesized nucleic acid. In certain aspects, the reaction mixture may provide the temperature suitable for hybridization between the template nucleic acid and the synthesized nucleic acid. For example, the reaction mixture may be heated to elute the synthesized nucleic acid from the first cylinder and subsequently cooled to a temperature suitable for hybridization between the template nucleic acid on the second cylinder and the synthesized nucleic acid.

In certain aspects, the first cylinder or the first region of the first cylinder may be heated to 60° C. to 100° C., from 65° C. to 95° C., from 70° C. to 90° C., or from 75° C. to 85° C., e.g., about 80° C. to synthesize the nucleic acid and to release the synthesized nucleic acid into the reaction mixture.

In certain aspects, the second cylinder or the first region of the second cylinder may be at to a temperature ranging from less than 60° C. to room temperature to facilitate hybridization between the template nucleic acid on the second cylinder and the synthesized nucleic acid. For example, the second cylinder may be heated to a temperature between 30° C. to 55° C., between 35° C. to 55° C., between 35° C. to 50° C., between 40° C. to 55° C., or between 40° C. to 50° C. to facilitate hybridization between the template nucleic acid on the second cylinder and the synthesized nucleic acid.

In certain aspects, the temperature suitable for hybridization between the template nucleic acid and the synthesized nucleic acid may be determined based on the nucleotide sequence of the template nucleic acid and the synthesized nucleic acid. Melting temperature and/or hybridization temperature may be calculated by methods known in the art and may be used for elution of the synthesized nucleic acid from the first cylinder and capture of the synthesized nucleic acid by the second cylinder, respectively.

Subsequently to the step of capturing the synthesized nucleic acid on the first surface of the second cylinder, the method involves recovering the synthesized nucleic acid by submerging the first portion of the outer surface of the second cylinder into a liquid under conditions sufficient for release of the captured synthesized nucleic acid into the liquid. The conditions sufficient for release of the captured synthesized nucleic acid into the liquid may include high temperature and/or chaotropic agents that decrease hybridization between the template nucleic acid and the captured synthesized nucleic acid. For example, the second cylinder or at least the first region of the second cylinder may be submerged into a nucleic acid elution liquid and either the liquid or the cylinder or both heated to release the captured synthesized nucleic acid into the liquid. Alternatively, or in addition, the nucleic acid elution liquid may include agents that decrease nucleic acid hybridization. For example, the nucleic acid elution liquid may include chaotropic agents, such as salts that denature the duplex formed by the template nucleic acid and the synthesized nucleic acid. Examples of chaotropic agents include urea, salts of guanidinium or guanidine, e.g., guanidinium hydrochloride. The second cylinder may be moved to a reservoir containing the nucleic acid elution liquid or the reaction mixture may be replaced with the nucleic acid elution liquid. The second cylinder or at least a portion (e.g., the first portion) may be submerged into the nucleic acid elution liquid for the recovering step. In certain aspects, the volume of the nucleic acid elution liquid may be low such that only a portion of the second cylinder can be submerged in the liquid. The recovering of the synthesized nucleic acid in such aspects may involve rotating the second cylinder to submerge a portion of the cylinder in the nucleic acid elution liquid.

The eluted synthesized nucleic acid may be concentrated by methods known in the art, such as, by filtration or precipitation, e.g., ethanol precipitation.

In certain aspects, the method includes rotating the second cylinder about its axis of radial symmetry a plurality of times such that the first portion of the outer surface of the second cylinder rotates into and out of the reaction mixture. The number of rotations may be sufficient to capture majority of the synthesized nucleic acid.

In certain aspects, the template nucleic acid is covalently attached to a plurality of portions of the outer surface of the second cylinder. In other words, the template nucleic acid is not localized to only a first portion of the outer surface of the second cylinder and the method includes rotating the second cylinder about its axis of radial symmetry a plurality of times such that the plurality of portions of the outer surface of the second cylinder rotate into and out of the reaction mixture. The template nucleic acid may be attached to two or three or more portions of the second cylinder. The template nucleic acid may be attached to a plurality of locations on the outer surface of the cylinder, e.g., may be disposed uniformly on the outer surface of the cylinder. For recovering the captures synthesized nucleic acid, the second cylinder or a portion thereof may be submerged in the nucleic acid elution liquid, as explained above and optionally rotated, e.g., when the volume of the nucleic acid elution liquid is insufficient to submerge the entire cylinder.

The capturing step may be performed after the synthesis of the nucleic acid is complete, or may be performed after each synthesis cycle, e.g., after every rotation of the first cylinder, or after a predetermined number of rotations of the first cylinder. In certain aspects, both the first and second cylinders may be rotated by a single motor. In certain aspects, a single motor may simultaneously rotate the first and second cylinders.

The present disclosure also provide methods for synthesizing sense and antisense strands which are hybridized to generate a double stranded nucleic acid, such as, double stranded DNA or double stranded RNA, e.g., siRNA. In certain aspects, the template nucleic acid described in the preceding paragraphs is a first template nucleic acid comprising a first sequence and the synthesized nucleic acid is a first synthesized nucleic acid comprising a sequence complementary to the first sequence, and the method further comprises synthesizing a second nucleic acid complementary to the first synthesized nucleic acid. In certain aspects, the method includes submerging a first portion of the outer surface of a third cylinder in a non-enzymatic nucleic acid synthesis reaction mixture as provided herein, wherein the first portion comprises a second template nucleic acid covalently attached thereto, wherein the sequence of the second template nucleic acid is complementary to the sequence of the first template nucleic acid attached to the first cylinder, wherein the reaction mixture has a pH of 4 or less and comprises an organizing matrix reagent and monophosphate nucleotides. The method further includes rotating the cylinder about its axis of radial symmetry so that the first portion of the outer surface of the third cylinder is no longer submerged in the reaction mixture, thereby providing a thin film of the reaction mixture on the first portion of the outer surface of the third cylinder; and heating and drying the thin film to form phosphodiester bonds between the monophosphate nucleotides of the thin film. The method further includes subsequent to the heating and drying, re-submerging the first portion of the outer surface of the third cylinder into the reaction mixture to release the synthesized second nucleic acid into the reaction mixture. These aspects of the method are similar to those described above in the context of the cylinder, e.g., the first cylinder used for synthesizing a nucleic acid.

The method further includes capturing the synthesized second nucleic acid from the reaction mixture by submerging a first portion of the outer surface of a fourth cylinder into the reaction mixture, wherein the first portion of the outer surface of the fourth cylinder comprises the second template nucleic acid covalently attached thereto, wherein the fourth cylinder is at a temperature suitable for hybridization between the second template nucleic acid and the second synthesized nucleic acid to capture the second synthesized nucleic acid. These aspects of the method are similar to those described above in the context of the second cylinder.

The method further includes recovering the second synthesized nucleic acid by submerging the first portion of the outer surface of the fourth cylinder into a liquid under conditions sufficient for release of the captured second synthesized nucleic acid into the liquid. These aspects of the method are similar to those described above in the context of the second cylinder.

The method further includes hybridizing the recovered first and second synthesized nucleic acids to obtain a double stranded synthesized nucleic acid. In certain aspects, the steps recovering and hybridizing may be performed by using a single nucleic acid elution liquid into which both of the synthesized sense and anti-sense strands are eluted, hybridized, and optionally concentrated. In other aspects, the eluted strands may be mixed under hybridization conditions to generate a duplex, such as, dsRNA, e.g., siRNA.

In certain aspects, the reaction mixture in which the first and second cylinders are submerged and re-submerged is physically separated from the reaction mixture in which the third and fourth cylinders are submerged and re-submerged. In other aspects, the first, second, third and fourth cylinders are submerged and re-submerged into a reaction mixture present in a single reservoir.

The template nucleic acid encoding a sense (or an anti-sense strand) strand present on the first and second cylinders, i.e., the synthesis cylinder and the recovery cylinder may have the same or substantially same nucleotide sequence. For example, both template nucleic acids may include a stretch of at least 10 nucleotides that are at least 80% identical in sequence. The template nucleic acid encoding a sense (or an anti-sense strand) strand present on the third and fourth cylinders, i.e., the synthesis cylinder and the recovery cylinder may have the same or substantially same nucleotide sequence. For example, both template nucleic acids may include a stretch of at least 10 nucleotides that are at least 80% identical in sequence. In other words, a 100% identity is not required for hybridization of the synthesized nucleic acid to the template nucleic acid present on the recovery cylinder.

The sense and anti-sense strands synthesized based on the respective template nucleic acids may include a region that forms a duplex with 3' overhangs, e.g., a duplex 19 to 25 bp in length with 3' dinucleotide overhangs.

As used herein, template nucleic acid encompasses plurality of such template nucleic acids, i.e., many copies of the template nucleic acid and synthesized nucleic acid encompasses plurality of such synthesized nucleic acids, i.e., many copies of the synthesized nucleic acid.

Devices

As summarized above, the present disclosure also provides devices for non-enzymatic nucleic acid synthesis. The devices find use in a variety of applications, including in practicing any of the methods of the present disclosure.

The devices of the present disclosure include a cylinder, a motor operably coupled to the cylinder and adapted to rotate the cylinder about its axis of radial symmetry, and a reservoir area positioned relative to the cylinder such that, when the device is in use, at least a portion of the outer surface of the cylinder may be submerged in a reaction mixture present in a reservoir present at the reservoir area. In certain aspects, the device includes a reservoir positioned relative to the cylinder such that, when the device is in use, at least a portion of the outer surface of the cylinder may be submerged in a reaction mixture present in the reservoir. The devices further include a heating device adapted to heat at least a portion of the cylinder that is not submerged in the reaction mixture, and a hermetically sealable chamber configured to house the cylinder, the reservoir, at least a portion of the motor, and at least a portion of the heating device.

As used throughout the present disclosure, a "cylinder" is a substantially radially symmetrical cylinder, e.g., a cylinder having 80% or greater, 85% or greater, 90% or greater, 95% or greater, 98% or greater, or 99% or greater radial symmetry.

The diameter and height of the cylinder may vary. In some embodiments, the diameter of the cylinder is from 1 cm to 100 cm, such as from 1 cm to 75 cm, from 1 cm to 50 cm, from 1 cm to 40 cm, from 1 cm to 30 cm, from 1 cm to 25 cm, from 1 cm to 20 cm, from 1 cm to 15 cm, from 1 cm to 10 cm, or from 1 cm to 5 cm. In certain aspects, the height of the cylinder—which may be in combination with any of the preceding diameter ranges—is from 1 cm to 100 cm, such as from 1 cm to 75 cm, from 1 cm to 50 cm, from 1 cm to 40 cm, from 1 cm to 30 cm, from 1 cm to 25 cm, from 1 cm to 20 cm, from 1 cm to 15 cm, from 1 cm to 10 cm, or from 1 cm to 5 cm.

The cylinder may be sized to have a selected lateral surface area, which may be determined by the equation $L=2\pi rh$, where L is the lateral surface area, r is the radius of the cylinder, and h is the height (or length when viewed horizontally) of the cylinder. The lateral surface area may be selected to provide a desired yield of synthesized nucleic acids when the device is in use, where a greater lateral surface area may be selected/exploited to obtain a greater yield of synthesized nucleic acids as compared to the yield obtained using a cylinder having a relatively lesser lateral surface area.

The one or more components of the cylinder may be made of any suitable material. In some embodiments, the outer surface of the cylinder includes a material selected from metal, glass, ceramic, a polymer, plastic, and any combination thereof.

The motor is operably coupled to the cylinder in a manner such that the motor may rotate the cylinder about its axis of radial symmetry. In some embodiments, the motor includes a rotatable element coupled to the cylinder at or near the central axis of the cylinder such that when the rotatable element of the motor is rotated, the motor rotates the cylinder about its axis of radial symmetry.

Various types of motors may be employed. In certain aspects, the motor is adapted to continuously and/or discontinuously rotate the cylinder through one or any desired number of revolutions. The motor of the device may be constructed to rotate the cylinder at a single rotational speed. In other aspects, the motor is a variable speed motor adapted to rotate the cylinder within a range of rotatable speeds selectable by a user of the device. In some embodiments, the motor is a clock motor. In certain aspects, the motor is adapted to rotate the cylinder at a rotational speed of from 1 revolution per 10 minutes to 1 revolution per 180 minutes, from 1 revolution per 20 minutes to 1 revolution per 120 minutes, from 1 revolution per 30 minutes to 1 revolution per 90 minutes, from 1 revolution per 40 minutes to 1 revolution per 80 minutes, or from 1 revolution per 50 minutes to 1 revolution per 70 minutes, e.g., 1 revolution per about 1 hour.

The reservoir area is adapted (e.g., sized) to support a reservoir of sufficient size to accommodate lowering of the cylinder into the reservoir when in use, e.g., to submerge at least a portion of the outer surface of the cylinder in a reaction mixture present in the reservoir. In some embodiments, the reservoir area is located on the bottom surface (or "floor") of the hermetically sealable chamber and includes in indentation in the bottom surface which is complementary to a reservoir to be used when the device is in operation. Such an indentation finds use, e.g., to facilitate proper alignment of the reservoir with the cylinder. When the device is provided with a reservoir, the size of the reservoir is sufficient to accommodate submersion of an outer surface of the cylinder in a reaction mixture present in the reservoir to a desired depth when the device is in use. The reservoir may be shaped to optimize the volume of the reaction mixture into which at least a portion of the cylinder(s) can be submerged. For example, the surface area of the reservoir may be reduced to a size sufficient to accommodate the length and width of the cylinder(s) and thereby increasing the depth reaction mixture available for submersion.

The heating device is adapted to heat at least a portion of the cylinder that is not submerged in the reaction mixture when the device is in use. In some embodiments, the heating device includes a heating element disposed adjacent the outer surface of the cylinder, where the heating element is disposed on the side opposite the thin film from the outer surface of the cylinder when the device is in use. Alternatively, or additionally, the heating element may be disposed adjacent (e.g., in contact with or disposed in sufficient proximity to) the inner surface of the cylinder, such that when the device is in use, the heating element heats the inner surface of the cylinder, which heat is conducted to the outer surface of the cylinder to heat a thin film of a reaction mixture disposed thereon.

In some embodiments, a device of the present disclosure further includes one or more gas ports. For example, the hermetically sealable chamber may include one or more walls that include one or more gas ports integrated therein. The gas ports find use, e.g., for flowing a gas (e.g., $CO_2$, an inert gas such as nitrogen gas, argon gas, helium gas, and/or the like) into the chamber to create an anaerobic environment within the chamber when the device is in use.

The hermetically sealable chamber is configured (e.g., sized) to house the cylinder, the reservoir area, at least a portion of the motor, and at least a portion of the heating element. In certain aspects, the hermetically sealable chamber has walls adapted to be coupled to one another such that the chamber is hermetically sealed. In some embodiments, the hermetically sealable chamber includes one or more transparent walls which enable a user to monitor a non-enzymatic synthesis reaction occurring therein when the device is in use. For example, the one or more transparent walls enable a user to monitor the depth of a reaction mixture present in the reservoir, the depth at which the outer surface of the cylinder is submerged in the reaction mixture, the state (e.g., wet or dry) of a thin film of the reaction mixture on the outer surface of the cylinder, and/or the like.

The device may include multiple cylinders. For example, the device may include a first and a second cylinder as described in the context of the methods of the present disclosure. The first and second cylinders may be made from the same or different materials. The outer surface of the second cylinder comprises a material selected from the group consisting of: metal, glass, ceramic, a polymer, plastic, and any combination thereof. In certain aspects, both first cylinder and the second cylinder are substantially radially symmetrical cylinders, wherein the reservoir area is positioned relative to the first and second cylinders such that, when the device is in use, at least a portion of the outer surface of the first and second cylinders is submerged in the reaction mixture present in the reservoir area.

In certain aspects, the reservoir area is a first reservoir area and the device comprises a second reservoir area and wherein the second cylinder is transferable between the first and second reservoir areas. The second reservoir area may include a nucleic acid elution liquid as described above.

The second cylinder may be connected to the same motor as the first cylinder or the device may include a second motor for rotating the second cylinder through one or more revolutions. The motor is adapted to rotate the second cylinder continuously through one or more revolutions. In certain aspects, the motor is adapted to rotate the second cylinder at a rotational speed of 1 revolution per 30 minutes to 1 revolution per 90 minutes. In certain aspects, the motor is adapted to rotate the second cylinder at a rotational speed of about 1 revolution per hour.

In certain aspects, the first cylinder is functionalized for covalent attachment of a template nucleic acid thereto. In certain aspects, a plurality of portions of the outer surface of the first cylinder is functionalized for covalent attachment of a template nucleic acid thereto.

In certain aspects, a first portion of the outer surface of the second cylinder is functionalized for covalent attachment of a template nucleic acid thereto. In certain aspects, a plurality of portions of the outer surface of the second cylinder is functionalized for covalent attachment of a template nucleic acid thereto.

In certain aspects, a first portion of the outer surface of the first cylinder comprises a template nucleic acid covalently attached thereto and a first portion of the second cylinder comprises a template nucleic acid covalently attached thereto, wherein the template nucleic acid attached to the first cylinder and the template nucleic acid attached to the second cylinder have substantially identical sequences. As used herein, substantially identical sequences refer to sequences comprising a contiguous stretch of at least 8 or more identical nucleotides. In certain aspects, two sequences are said to be substantially identical when they have an identity of at least 80% or more, e.g., 90% or 95%. In certain aspects, the sequences may be identical, i.e., have a 100% identity.

In certain aspects, a plurality of portions of the outer surface of the first cylinder comprises a template nucleic acid covalently attached thereto and a plurality of portions of the outer surface of the second cylinder comprises a template nucleic acid covalently attached thereto, wherein the template nucleic acid attached to the first cylinder and the template nucleic acid attached to the second cylinder have substantially identical sequences.

A photograph of a device according to one embodiment of the present disclosure is provided in FIG. 1. In this example, the device includes a reservoir for containing a liquid such as a non-enzymatic nucleic acid synthesis reaction mixture, and a cylinder lowered into the reservoir such that the outer surface of the cylinder is submerged at a desired depth in the reaction mixture, when present. The device includes a chamber having walls which are joined to form hermetic seals such that an anaerobic environment may be created within the chamber. Integrated in the left wall is a clock motor having a motor portion external to the chamber and a rotatable element that protrudes into the chamber for coupling to the cylinder at its central axis such that when the rotatable element of the motor is rotated, the motor rotates the cylinder about its axis of radial symmetry. In this example, the motor is adapted to rotate the cylinder at a rotational speed of about 1 revolution per hour. Integrated into the right wall is a heating device having a heating element that protrudes into the chamber for thermally coupling to the inner surface of the cylinder. In this example, the heating element is disposed within sufficient proximity to the inner surface of the cylinder to heat the inner surface of the cylinder, which heat is conducted to the outer surface of the cylinder to heat a thin film thereon when the device is in use. Also integrated into the right wall is a gas port through which gas (e.g., $CO_2$) may be flowed into the chamber for creating an anaerobic environment therein when the device is in use.

Figure 4:
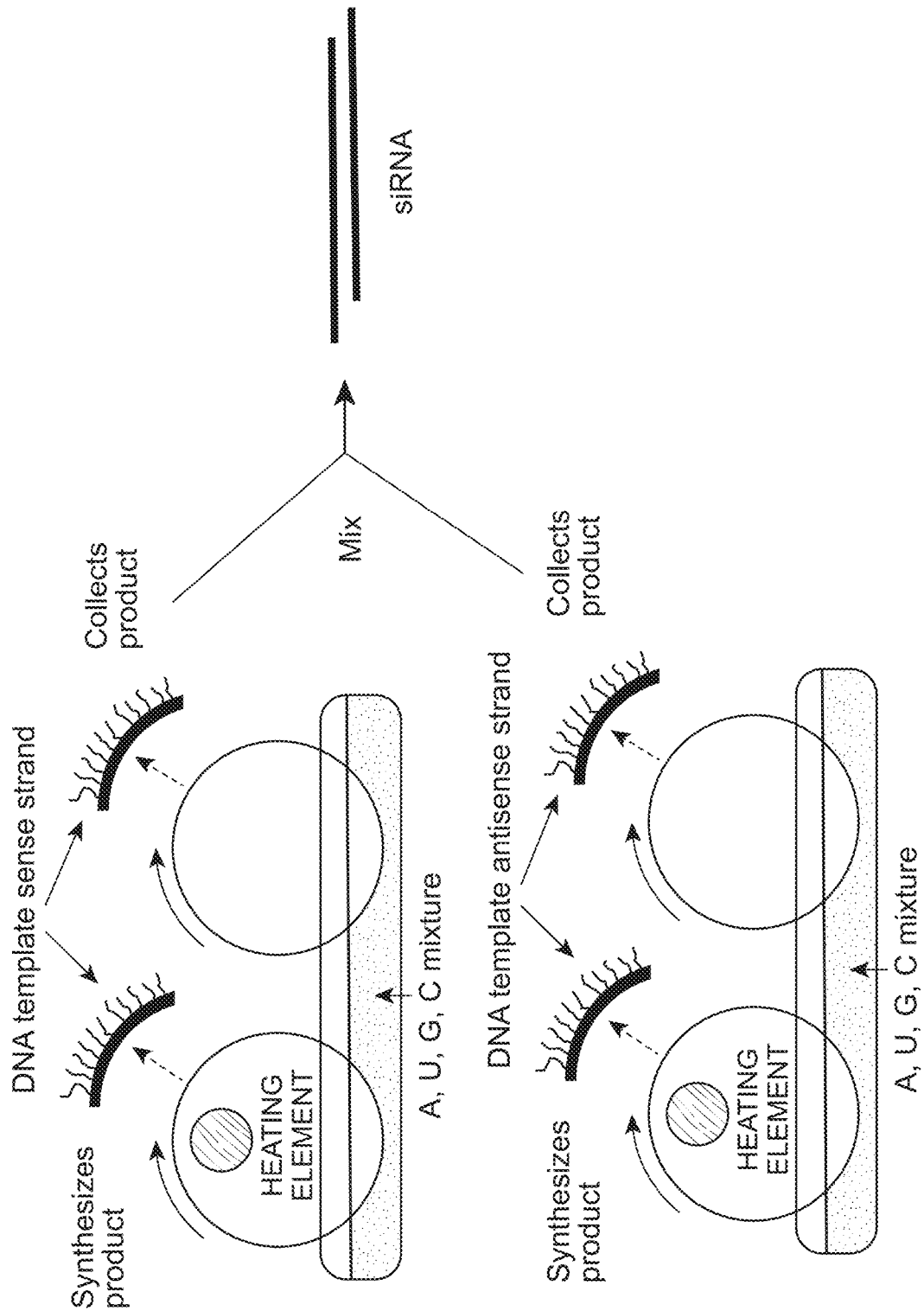
FIG. 4 Schematic of a device for non-enzymatic nucleic acid synthesis according to one embodiment of the present disclosure.

FIG. 4 shows two devices each device having the features described in FIG. 1 and each additionally includes a further cylinder for recovering the synthesized nucleic acid. The recovered nucleic acids are sense and anti-sense strands that are mixed to generate a double stranded nucleic acid such as a siRNA.

Notwithstanding the appended claims, the present disclosure is also defined by the following embodiments:

1. A method for non-enzymatically synthesizing nucleic acids, comprising:
    submerging a first portion of the outer surface of a cylinder in a non-enzymatic nucleic acid synthesis reaction mixture, wherein the reaction mixture has a pH of 4 or less and comprises an organizing matrix reagent and monophosphate nucleotides;
    rotating the cylinder about its axis of radial symmetry so that the first portion of the outer surface of the cylinder is no longer submerged in the reaction mixture, thereby providing a thin film of the reaction mixture on the first portion of the outer surface of the cylinder; and
    heating and drying the thin film to form phosphodiester bonds between the monophosphate nucleotides of the thin film.

2. The method according to embodiment 1, wherein the submerging comprises rotating the cylinder about its axis of radial symmetry such that the first portion of the outer surface of the cylinder rotates into the reaction mixture.

3. The method according to embodiment 1 or embodiment 2, further comprising, subsequent to the heating and drying, re-submerging the first portion of the outer surface of the cylinder in the reaction mixture.

4. The method according to embodiment 3, wherein the re-submerging comprises rotating the cylinder about its axis of radial symmetry such that the first portion of the outer surface of the cylinder rotates into the reaction mixture.

5. The method according to any one of embodiments 1 to 4, wherein the cylinder is rotated through one or more revolutions.

6. The method according to embodiment 5, wherein the cylinder is rotated continuously through one or more revolutions.

7. The method according to embodiment 5 or embodiment 6, wherein the cylinder is rotated at a rotational speed of 1 revolution per 30 minutes to 1 revolution per 90 minutes.

8. The method according to embodiment 5 or embodiment 6, wherein the cylinder is rotated at a rotational speed of about 1 revolution per hour.

9. The method according to any one of embodiments 1 to 8, wherein the cylinder is submerged in the reaction mixture at a depth of about 5% to 20% of the diameter of the cylinder.

10. The method according to any one of embodiments 1 to 9, wherein the reaction mixture has a pH of from 2 to 4.

11. The method according to any one of embodiments 1 to 10, wherein the organizing matrix reagent comprises one or more amphiphilic compounds.

12. The method according to embodiment 11, wherein the one or more amphiphilic compounds are selected from the group consisting of: phospholipids, lysophosphatidylcholine, mixtures of dodecanoic acid with its monoglyceride, and any combination thereof.

13. The method according to embodiment 11 or embodiment 12, wherein the one or more amphiphilic compounds are present in the reaction mixture at a mass ratio of from 1.5:1 to 2.5:1 monophosphate nucleotides:amphiphilic compounds.

14. The method according to any one of embodiments 1 to 13, wherein the organizing matrix reagent comprises one or more monovalent salts.

15. The method according to embodiment 14, wherein the one or more monovalent salts comprises a halide salt.

16. The method according to embodiment 15, wherein the halide salt is an ammonium halide salt.

17. The method according to embodiment 16, wherein the ammonium halide salt is ammonium chloride ($NH_4Cl$).

18. The method according to embodiment 14, wherein the one or more monovalent salts are selected from the group consisting of: NaF, CsCl, NaBr, $NaClO_4$, NaCl, KCl, $NH_4Cl$, and any combination thereof.

19. The method according to any one of embodiments 15 to 18, wherein the one or more monovalent salts are present in the reaction mixture at a concentration of from 0.05 M to 2 M.

20. The method according to any one of embodiments 1 to 19, wherein heating the thin film comprises heating the inner surface of the cylinder.

21. The method according to embodiment 20, wherein the inner surface of the cylinder is heated using a heating element thermally coupled to the inner surface of the cylinder.

22. The method according to any one of embodiments 1 to 21, wherein the thin film is heated during evaporation and drying on the cylinder at a temperature of from 70° C. to 90° C.

23. The method according to any one of embodiments 1 to 22, wherein drying the thin film comprises flowing a gas over the at least a portion of the outer surface of the cylinder.

24. The method according to any one of embodiments 1 to 23, wherein the non-enzymatic nucleic acid synthesis occurs on a nucleic acid template.

25. The method according to embodiment 24, wherein the reaction mixture comprises the template nucleic acid.

26. The method according to embodiment 24 or embodiment 25, wherein the first portion of the outer surface of the cylinder comprises the template nucleic acid disposed thereon.

27. The method according to any one of embodiments 1 to 26, wherein the nucleic acid to be synthesized is ribonucleic acid (RNA) and the reaction mixture comprises ribonucleotide monophosphates.

28. The method according to embodiment 27, wherein the nucleic acid to be synthesized is small interfering RNA (siRNA).

29. The method according to any one of embodiments 1 to 28, wherein the nucleic acid to be synthesized is deoxyribonucleic acid (DNA) and the reaction mixture comprises deoxyribonucleotide monophosphates.

30. The method according to any one of embodiments 1 to 29, further comprising recovering the synthesized nucleic acid from the first portion of the outer surface of the cylinder.

31. The method according to any one of embodiments 1 to 29, wherein the cylinder is a first cylinder and the template nucleic acid is covalently attached to the first portion of the outer surface of the first cylinder and wherein the method comprises:
   subsequent to the heating and drying, re-submerging the first portion of the outer surface of the cylinder in the reaction mixture to release the synthesized nucleic acid into the reaction mixture;
   capturing the synthesized nucleic acid from the reaction mixture by submerging a first portion of the outer surface of a second cylinder into the reaction mixture,
   wherein the first portion of the outer surface of the second cylinder comprises the template nucleic acid covalently attached thereto,
   wherein the second cylinder is at a temperature suitable for hybridization between the template nucleic acid and the synthesized nucleic acid to capture the synthesized nucleic acid; and
   recovering the synthesized nucleic acid by submerging the first portion of the outer surface of the second cylinder into a liquid under conditions sufficient for release of the captured synthesized nucleic acid into the liquid.

32. The method according to embodiment 31, wherein the method comprises rotating the second cylinder about its axis of radial symmetry a plurality of times such that the first portion of the outer surface of the second cylinder rotates into and out of the reaction mixture.

33. The method according to embodiment 31, wherein the template nucleic acid is covalently attached to a plurality of portions of the outer surface of the second cylinder.

34. The method according to embodiment 33, wherein the method comprises rotating the second cylinder about its axis of radial symmetry a plurality of times such that the plurality of portions of the outer surface of the second cylinder rotate into and out of the reaction mixture.

35. The method according to any one of embodiments 31 to 34, wherein the nucleic acid to be synthesized is ribonucleic acid (RNA) and the reaction mixture comprises ribonucleotide monophosphates.

36. The method according to any one of embodiments 31 to 35, wherein the nucleic acid to be synthesized is deoxyribonucleic acid (DNA) and the reaction mixture comprises deoxyribonucleotide monophosphates.

37. The method according to any one of embodiments 31 to 36, wherein the template nucleic acid is a first template nucleic acid comprising a first sequence and the synthesized nucleic acid is a first synthesized nucleic acid comprising a sequence complementary to the first sequence, the method further comprising synthesizing a second nucleic acid complementary to the first synthesized nucleic acid, the method comprising;
   submerging a first portion of the outer surface of a third cylinder in a non-enzymatic nucleic acid synthesis reaction mixture, wherein the first portion comprises a second template nucleic acid covalently attached thereto, wherein the sequence of the second template nucleic acid is complementary to the sequence of the first template nucleic acid attached to the first cylinder, wherein the reaction mixture has a pH of 4 or less and comprises an organizing matrix reagent and monophosphate nucleotides;
   rotating the cylinder about its axis of radial symmetry so that the first portion of the outer surface of the third cylinder is no longer submerged in the reaction mixture, thereby providing a thin film of the reaction mixture on the first portion of the outer surface of the third cylinder; and
   heating and drying the thin film to form phosphodiester bonds between the monophosphate nucleotides of the thin film.

38. The method according to embodiment 37, further comprising:
   subsequent to the heating and drying, re-submerging the first portion of the outer surface of the third cylinder into the reaction mixture to release the synthesized second nucleic acid into the reaction mixture;
   capturing the synthesized second nucleic acid from the reaction mixture by submerging a first portion of the outer surface of a fourth cylinder into the reaction mixture,
   wherein the first portion of the outer surface of the fourth cylinder comprises the second template nucleic acid covalently attached thereto,
   wherein the fourth cylinder is at a temperature suitable for hybridization between the second template nucleic acid and the second synthesized nucleic acid to capture the second synthesized nucleic acid;
   recovering the second synthesized nucleic acid by submerging the first portion of the outer surface of the fourth cylinder into a liquid under conditions sufficient for release of the captured second synthesized nucleic acid into the liquid; and
   hybridizing the first and second synthesized nucleic acids to obtain a double stranded synthesized nucleic acid.

39. The method according to embodiment 37 or embodiment 38, wherein the first and second synthesized nucleic acids are ribonucleic acids and the reaction mixture comprises ribonucleotide monophosphates.

40. The method according to embodiment 37 or embodiment 38, wherein the first and second synthesized nucleic acids are deoxyribonucleic acids and the reaction mixture comprises deoxyribonucleotide monophosphates.

41. The method according to any one of embodiments 37 to 40, wherein the reaction mixture in which the first and second cylinders are submerged and re-submerged is physically separated from the reaction mixture in which the third and fourth cylinders are submerged and re-submerged.

42. The method according to any one of embodiments 37 to 41, wherein the liquid into which the first synthesized nucleic acid is released is the same liquid into which the second synthesized nucleic acid is released.

43. The method according to any one of embodiments 31 to 42, wherein the liquid into which synthesized nucleic acid is released is water or a solution.

44. The method according to 43, wherein the solution is a salt solution.

45. The method according to 43, wherein the solution is a buffer.

46. A device for non-enzymatic nucleic acid synthesis, comprising:
   a substantially radially symmetrical cylinder;
   a motor operably coupled to the cylinder and adapted to rotate the cylinder about its axis of radial symmetry;
   a reservoir area positioned relative to the cylinder such that, when the device is in use, at least a portion of the outer surface of the cylinder may be submerged in a reaction mixture present in a reservoir present at the reservoir area;
   a heating device adapted to heat at least a portion of the cylinder that is not submerged in the reaction mixture; and
   a hermetically sealable chamber configured to house the cylinder, the reservoir area, at least a portion of the motor, and at least a portion of the heating element.

47. The device according to embodiment 46, wherein the outer surface of the cylinder comprises a material selected from the group consisting of: metal, glass, ceramic, a polymer, plastic, and any combination thereof.

48. The device according to embodiment 46 or embodiment 47, wherein the motor is adapted to rotate the cylinder through one or more revolutions.

49. The device according to any one of embodiments 46 to 48, wherein the motor is adapted to rotate the cylinder continuously through one or more revolutions.

50. The device according to any one of embodiments 46 to 49, wherein the motor is adapted to rotate the cylinder at a rotational speed of 1 revolution per 30 minutes to 1 revolution per 90 minutes.

51. The device according to any one of embodiments 46 to 49, wherein the motor is adapted to rotate the cylinder at a rotational speed of about 1 revolution per hour.

52. The device according to any one of embodiments 46 to 51, wherein the motor is a clock motor.

53. The device according to any one of embodiments 46 to 52, wherein the heating device comprises a heating element disposed internally to the cylinder for heating the inner surface of the cylinder.

54. The device according to any one of embodiments 46 to 53, further comprising a gas port in a wall of the hermetically sealable chamber.

55. The device according to any one of embodiments 46 to 54, wherein the hermetically sealable chamber comprises walls comprising plastic or glass.

56. The device according to any one of embodiments 46 to 55, wherein the cylinder is a first cylinder and wherein the device comprises a second substantially radially symmetrical cylinder, wherein the reservoir area is positioned relative to the second cylinder such that, when the device is in use, at least a portion of the outer surface of the second cylinder may be submerged in a reaction mixture present in a reservoir area.

57. The device according to any one of embodiments 46 to 55, wherein the reservoir area is first reservoir area and the device comprises a second reservoir area and wherein the second cylinder is transferable between the first and second reservoir area.

58. The device according to embodiment 56 or embodiment 57, wherein the outer surface of the second cylinder comprises a material selected from the group consisting of: metal, glass, ceramic, a polymer, plastic, and any combination thereof.

59. The device according to any one of embodiments 56 to 58, wherein the motor is adapted to rotate the second cylinder through one or more revolutions.

60. The device according to any one of embodiments 56 to 58, wherein the motor is adapted to rotate the second cylinder continuously through one or more revolutions.

61. The device according to any one of embodiments 56 to 60, wherein the motor is adapted to rotate the second cylinder at a rotational speed of 1 revolution per 30 minutes to 1 revolution per 90 minutes.

62. The device according to any one of embodiments 56 to 61, wherein the motor is adapted to rotate the second cylinder at a rotational speed of about 1 revolution per hour.

63. The device according to any one of embodiments 56 to 62, wherein the device comprises a second motor adapted to rotate the second cylinder through one or more revolutions.

64. The device according to any one of embodiments 46 to 62, wherein a first portion of the outer surface of the first cylinder is functionalized for covalent attachment of a template nucleic acid thereto.

65. The device according to any one of embodiments 46 to 62, wherein a plurality of portions of the outer surface of the first cylinder is functionalized for covalent attachment of a template nucleic acid thereto.

66. The device according to any one of embodiments 56 to 65, wherein a first portion of the outer surface of the second cylinder is functionalized for covalent attachment of a template nucleic acid thereto.

67. The device according to any one of embodiments 56 to 65, wherein a plurality of portions of the outer surface of the second cylinder is functionalized for covalent attachment of a template nucleic acid thereto.

68. The device according to any one of embodiments 56 to 67, wherein a first portion of the outer surface of the first cylinder comprises a template nucleic acid covalently attached thereto and a first portion of the second cylinder comprises a template nucleic acid covalently attached thereto, wherein the template nucleic acid attached to the first cylinder and the template nucleic acid attached to the second cylinder have substantially identical sequences.

69. The device according to any one of embodiments 56 to 67, wherein a plurality of portions of the outer surface of the first cylinder comprises a template nucleic acid covalently attached thereto and a plurality of portions of the outer surface of the second cylinder comprises a template nucleic acid covalently attached thereto, wherein the template nucleic acid attached to the first cylinder and the template nucleic acid attached to the second cylinder have substantially identical sequences.

The following examples are offered by way of illustration and not by way of limitation.

EXPERIMENTAL

Example 1

Continuous Mode Device for Non-Enzymatic Nucleic Acid Synthesis

Described in this example is a continuous mode device for exposing a solution of mononucleotides to cycles of hydration and dehydration.

For the reaction mixture, a 10 mM solution of nucleotides was prepared in its protonated form. Because these are acids, the pH of the solution was 2.5. An acidic pH (e.g., pH 4 or lower) is required because ester bond synthesis is an acid-catalyzed Fisher esterification. The nucleotide in this particular example was thymidine monophosphate (TMP). Any of a variety of amphiphilic compounds is then added to the mixture in a mass ratio of 2:1 nucleotides:amphiphiles. Examples of amphiphiles include phospholipids, lysophosphatidylcholine, or mixtures of dodecanoic acid with its monoglyceride. All of these amphiphiles share the property of forming multilamellar matrices when dried. Lysophosphatidylcholine was used as the amphiphile in this particular example (De Guzman et al. (2014) *J Mol Evol.* 78:251-62). In a second experiment, 0.1 M ammonium chloride ($NH_4Cl$) was used as the organizing matrix reagent to produce a eutectic phase when crystals form that promote polymerization (Da Silva et al. (2015) *J Mol Evol.* 80, 86-97). In this example, a DNA template was provided such that the non-enzymatic nucleic acid synthesis was templated.

A continuous mode device as shown in FIG. 1 was employed to expose the reaction mixture to continuous cycles of dehydration and rehydration at an elevated temperature to provide activation energy. As the amphiphiles become increasingly concentrated, they fuse into a multilamellar structure that concentrates and organizes the nucleotides and template into a two dimensional reaction space of a liquid crystalline matrix. If $NH_4Cl$ is used as the organizing matrix reagent, the reactants are concentrated into a eutectic phase that causes them to form stacks called prepolymers (Himbert et al. (2016) *Scientific Reports* 6:31285).

The nucleotides are able to diffuse, and as they become increasingly concentrated, water activity is sufficiently reduced to drive phosphoester bond synthesis. In this particular example, the continuous mode device exposed the reaction mixture to multiple one hour cycles. In one day, therefore, 24 reaction cycles would be completed. The product sequences accumulate in a kinetic trap because the hydrolysis reaction is much slower than the rate of synthesis.

After the run, the organizing matrix reagents may be removed and products are isolated by ethanol precipitation, Zymo spin tubes, or the like.

In this example, the cylinder of the continuous mode device is heated to a desired temperature by the heating element, and is rotated once an hour by a clock motor. As it rotates through a 15 mL reaction mixture, a thin film is picked up on the outer surface of the cylinder (in this example, a burnished stainless steel drum) which is dried by the temperature (80° C.) and flow of $CO_2$ through the chamber. As the water evaporates, a multilamellar film forms on the surface that captures the reactants within the organizing matrix where they undergo spontaneous polymerization. The film and products are then rehydrated as the cylinder rotation brings them back into the aqueous phase where they are released into solution. Previously, using cycles in batch mode and 0.1 to 0.2 mL volumes, yields were measured in a few micrograms, but yields of polymer products are in the milligram range with the continuous mode device.

Gel Electrophoresis of Products

Figure 2:
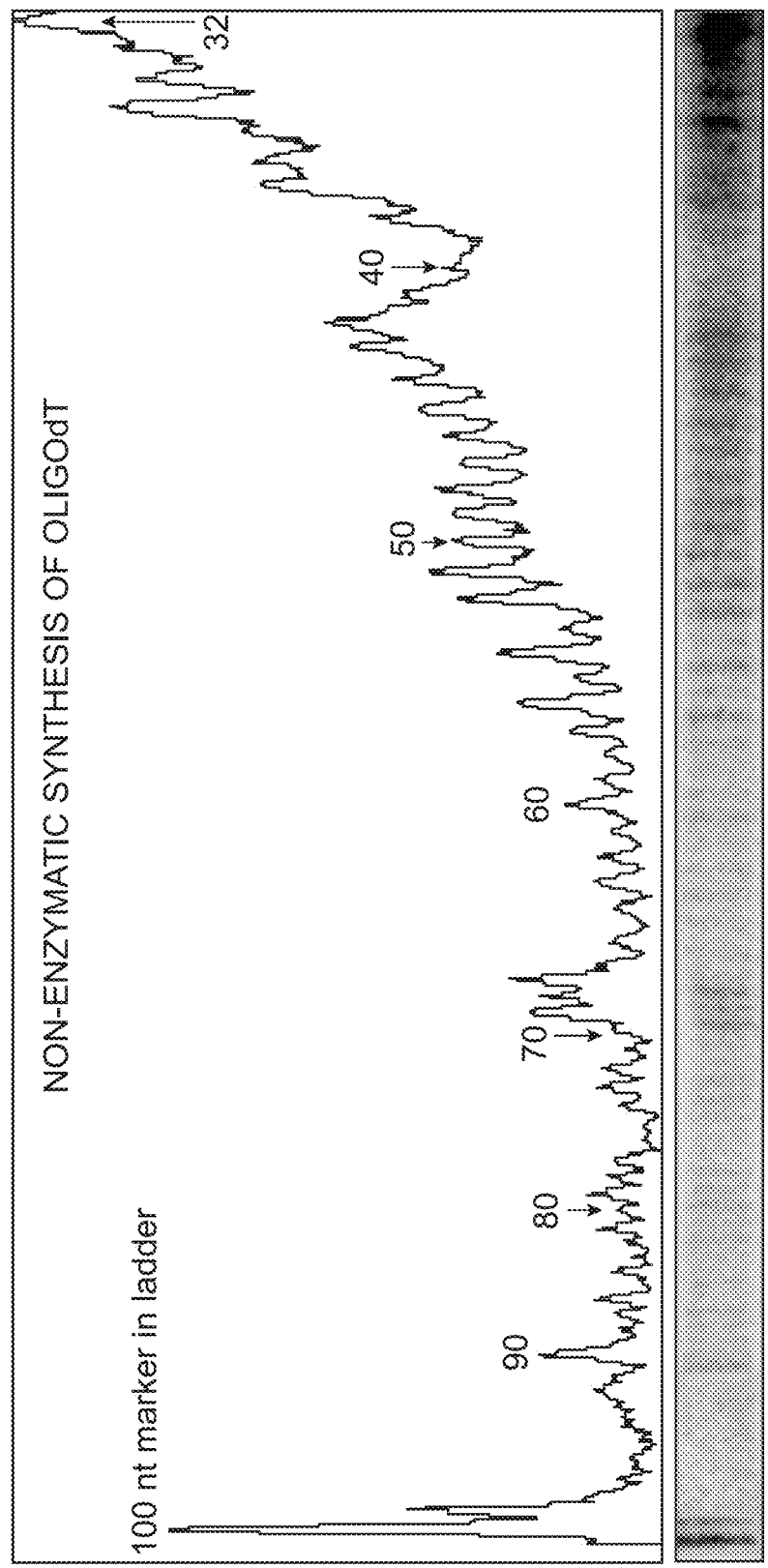
FIG. 2 Polyacrylamide gel analysis of nucleic acids synthesized according to one embodiment of the present disclosure.

In one example that used TMP as a monomer, a sequencing polyacrylamide gel was run after products were labeled with $^{32}P$ (FIG. 2). The lane shows the products of a run with $NH_4Cl$ present as the organizing matrix reagent. A 100 nt marker band of a ladder is indicated on the left. The products ranged in length, starting at ~30 nt and up to ~90 nt. In FIG. 2, the gel lane shows bands that have been labeled with $^{32}P$, and the image above the gel lane is a scan of the gel performed with Image J software.

Nanopore Analysis of the Base Sequence

Figure 3:
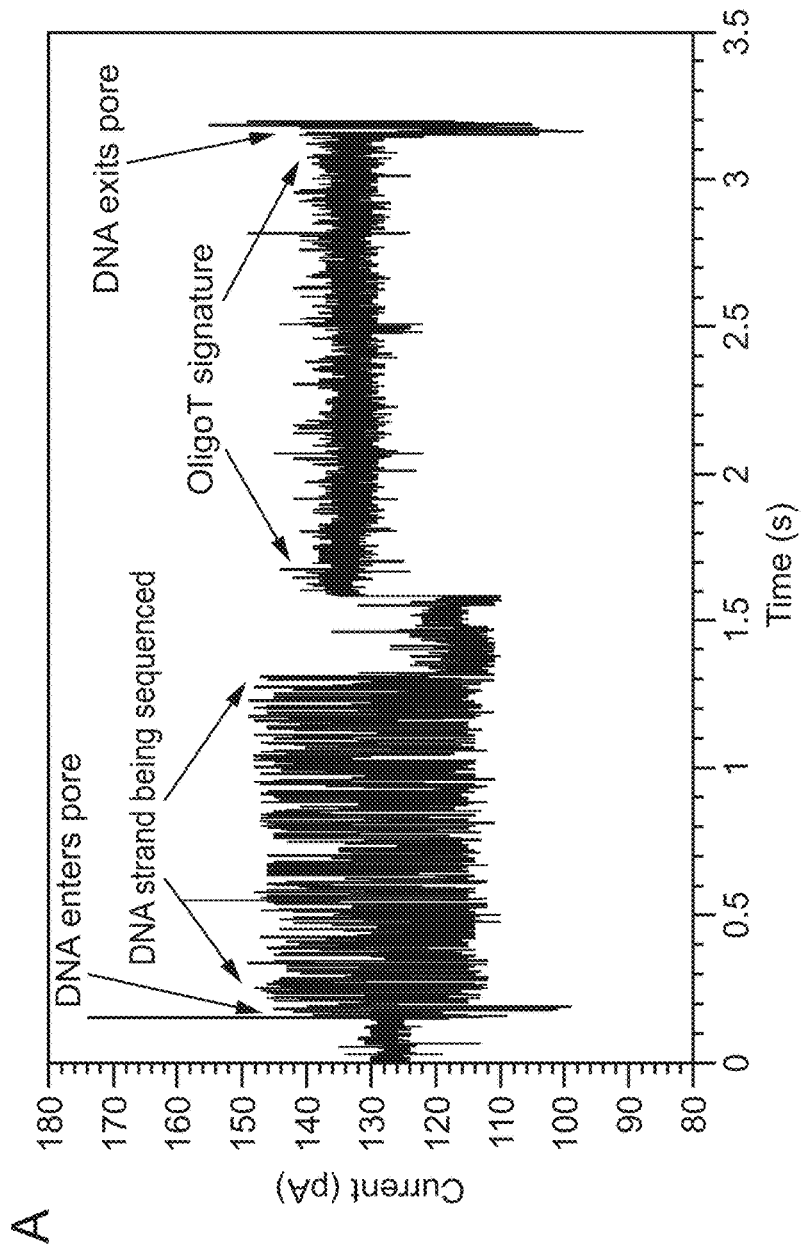
FIG. 3 Nanopore sequencing analysis of nucleic acids synthesized according to one embodiment of the present disclosure. Panel A: Electronic signature of a single molecule of DNA product translocating through a nanopore. Panel B: The signal from panel A was submitted for base calling, and two sequences are shown in panel B to illustrate the expected oligoT homopolymers (highlighted) followed by sequences marking the carrier DNA.

In another example using TMP, a nanopore-based sequencing run was performed on products synthesized with lysophosphatidylcholine used as the organizing matrix reagent. In this example, an Oxford Nanopore Technology MinION® sequencing device was used to perform the sequencing run. The isolated product nucleic acids were ligated to a known synthetic DNA sequence that would be recognized by the enzymes used to prepare DNA for MinION® sequencing device analysis. The nanopore signals showed the known DNA strand followed by a signature interpreted as the oligoT ligated to it. One example of such a signal is shown in FIG. 3, panel A. In this example, the electronic signature of a single molecule of DNA product translocating through one of 400 active pores shows the known DNA ligated to the oligomer product that was synthesized by the process. The signature interpreted as oligo T is that expected of a homopolymer.

The signal was submitted for base calling, and two sequences are shown below to illustrate the expected oligoT homopolymers (highlighted) followed by sequences marking the carrier DNA. The sequences are within the expected lengths revealed in the gel (FIG. 2).

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A method for non-enzymatically synthesizing a nucleic acid, comprising:

submerging in a non-enzymatic nucleic acid synthesis reaction, mixture a first portion of the outer surface of a first cylinder, wherein a template nucleic acid is covalently attached to the first portion of the outer surface of the first cylinder, and wherein the reaction mixture has a pH of 4 or less and comprises an organizing matrix reagent and monophosphate nucleotides;

rotating the first cylinder about its axis of radial symmetry so that the first portion of the outer surface of the first cylinder is no longer submerged in the reaction mixture, thereby providing a thin film of the reaction mixture on the first portion of the outer surface of the first cylinder;

heating and drying the thin film to form phosphodiester bonds between the monophosphate nucleotides of the thin film to produce the nucleic acid;

subsequent to the heating and drying, re-submerging the first portion of the outer surface of the first cylinder in the reaction mixture to release the nucleic acid into the reaction mixture;

capturing the nucleic acid from the reaction mixture by submerging into the reaction mixture a first portion of the outer surface of a second cylinder, wherein the first portion of the outer surface of the second cylinder comprises the template nucleic acid covalently attached thereto, and wherein the second cylinder is at a temperature suitable for hybridization between the template nucleic acid covalently attached to the first portion of the outer surface of the second cylinder and the nucleic acid released into the reaction mixture; and recovering the nucleic acid by submerging the first portion of the outer surface of the second cylinder into a liquid under conditions sufficient to release into the liquid the captured nucleic acid.

2. The method according to claim 1, wherein the submerging the first cylinder comprises rotating the first cylinder about its axis of radial symmetry such that the first portion of the outer surface of the first cylinder rotates into the reaction mixture.

3. The method according to claim 1, wherein the re-submerging the first portion of the outer surface of the first cylinder in the reaction mixture comprises rotating the first cylinder about its axis of radial symmetry such that the first portion of the outer surface of the first cylinder rotates into the reaction mixture.

4. The method according to claim 1, wherein the first cylinder is rotated continuously through one or more revolutions.

5. The method according to claim 4, wherein the first cylinder is rotated at a rotational speed of 1 revolution per 30 minutes to 1 revolution per 90 minutes.

6. The method according to claim 1, wherein the organizing matrix reagent comprises one or more amphiphilic compounds.

7. The method according to claim 6, wherein the one or more amphiphilic compounds are selected from the group consisting of: phospholipids, lysophosphatidylcholine, mixtures of dodecanoic acid with its monoglyceride, and any combination thereof.

8. The method according to claim 1, wherein the organizing matrix reagent comprises one or more monovalent salts.

9. The method according to claim 1, wherein heating the thin film comprises heating the inner surface of the first cylinder using a heating element thermally coupled to the inner surface of the cylinder.

10. The method according to claim 1, wherein the nucleic acid is ribonucleic acid (RNA) and the reaction mixture comprises ribonucleotide monophosphates.

11. The method according to claim 10, wherein the nucleic acid is small interfering RNA (siRNA).

12. The method according to claim 1, wherein the template nucleic acid is a first template nucleic acid comprising a first sequence and the nucleic acid is a first nucleic acid comprising a sequence complementary to the first sequence, the method further comprising synthesizing a second nucleic acid complementary to the first nucleic acid, the method comprising;

submerging a first portion of the outer surface of a third cylinder in a non-enzymatic nucleic acid synthesis reaction mixture, wherein the first portion of the outer surface of a third cylinder comprises a second template nucleic acid covalently attached thereto, wherein the sequence of the second template nucleic acid is complementary to the sequence of the first template nucleic acid attached to the first cylinder, wherein the reaction mixture has a pH of 4 or less and comprises an organizing matrix reagent and monophosphate nucleotides;

rotating the third cylinder about its axis of radial symmetry so that the first portion of the outer surface of the third cylinder is no longer submerged in the reaction mixture, thereby providing a thin film of the reaction mixture on the first portion of the outer surface of the third cylinder; and heating and drying the thin film to form phosphodiester bonds between the monophosphate nucleotides of the thin film.

* * * * *

UNITED STATES PATENT AND TRADEMARK OFFICE
CERTIFICATE OF CORRECTION

PATENT NO. : 12,325,011 B2  
APPLICATION NO. : 17/288356  
DATED : June 10, 2025  
INVENTOR(S) : David W. Deamer et al.

Page 1 of 1

It is certified that error appears in the above-identified patent and that said Letters Patent is hereby corrected as shown below:

In the Claims

In Column 25, Line 2, in Claim 1, delete "reaction," and insert -- reaction --.

Signed and Sealed this  
Second Day of September, 2025

Coke Morgan Stewart  
*Acting Director of the United States Patent and Trademark Office*